US010961246B2

(12) United States Patent
Schibli et al.

(10) Patent No.: US 10,961,246 B2
(45) Date of Patent: Mar. 30, 2021

(54) ¹⁸F-LABELLED FOLATES AS PET RADIOTRACERS

(71) Applicant: MERCK & CIE, Schaffhausen (CH)

(72) Inventors: Roger Schibli, Baden (CH); Rudolf Moser, Schaffhausen (CH); Cristina Magdalena Muller, Nussbaumen (CH); Simon Mensah Ametamey, Zurich (CH); Tobias Ludwig Ross, Zurich (CH); Viola Groehn, Dachsen (CH)

(73) Assignee: MERCK & CIE, Schaffhausen (CH)

( * ) Notice: Subject to any disclaimer, the term of this patent is extended or adjusted under 35 U.S.C. 154(b) by 198 days.

(21) Appl. No.: 15/711,316

(22) Filed: Sep. 21, 2017

(65) Prior Publication Data

US 2018/0072734 A1 Mar. 15, 2018

Related U.S. Application Data

(63) Continuation of application No. 13/123,329, filed as application No. PCT/EP2009/063258 on Oct. 12, 2009.

(30) Foreign Application Priority Data

Oct. 10, 2008 (EP) .................................... 08166356

(51) Int. Cl.
A61K 51/00 (2006.01)
A61M 36/14 (2006.01)
C07D 475/04 (2006.01)

(52) U.S. Cl.
CPC ................... C07D 475/04 (2013.01)

(58) Field of Classification Search
CPC .................................................... C07D 475/04
USPC ........................................................... 424/1.89
See application file for complete search history.

(56) References Cited

U.S. PATENT DOCUMENTS

| 4,202,976 A | 5/1980 | Bayly et al. |
| 4,276,280 A | 6/1981 | Akerkar et al. |
| 4,298,735 A | 11/1981 | Farina et al. |
| 4,314,988 A | 2/1982 | Farina et al. |
| 4,584,375 A | 4/1986 | Coward |
| 4,628,090 A | 12/1986 | Coward |
| 2010/0217011 A1 | 8/2010 | Dinkelborg et al. |

FOREIGN PATENT DOCUMENTS

| CA | 2667395 A1 | 5/2008 |
| EP | 491282 A2 | 6/1992 |
| EP | 0 451 835 B1 | 9/1995 |
| EP | 0 451 836 B1 | 12/1995 |
| GB | 1 501 119 | 2/1978 |
| JP | 61-044890 A | 3/1986 |
| WO | 2004/110500 A1 | 12/2004 |
| WO | WO-2006067376 A2 * | 6/2006 ........... A61K 51/088 |
| WO | 2006071754 A2 | 7/2006 |
| WO | 2008052788 A1 | 5/2008 |
| WO | 2008098112 A2 | 8/2008 |
| WO | 2008125613 A1 | 10/2008 |
| WO | 2008125615 A1 | 10/2008 |
| WO | 2008125617 A2 | 10/2008 |

OTHER PUBLICATIONS

International Search Report of PCT/EP2009/063258 (dated Dec. 17, 2009).
J. J. Mcguire et al., "Biochemical and Growth Inhibitory Effects of the Erythro and Threo Isomers of—Fluoromethotrexate, a Methotrexate Analogue Defective in Polyglutamylation", Cancer Research, vol. 49 (Aug. 15, 1989) pp. 4517-4525.
A. Bettio et al., "Synthesis and Preclinical Evaluation of a Folic Acid Derivative Labeled with 18F for PET Imaging of Folate Receptor-Positive Tumors", Journal of Nuclear Medicine, vol. 47 (2006) pp. 1153-1160.
C. Muller et al., "Dose-Dependent Effects of (Anti)Folate Preinjection on 99mTC-Radiofolate Uptake in Tumors and Kidneys", Nuclear Medicine and Biology, vol. 34 (2007) pp. 603-608.
J. Galivan et al., "gamma-Fluoromethotrexate: Synthesis and Biological Activity of a Potent Inhibitor of Dihydrofolate Reductase with Greatly Diminished Ability to Form Poly-gamma-Glutamates", Proc. Natl. Acad. Sci., vol. 82 (May 1985) pp. 2598-2602.
George et al., Biochem. 1987, 26, 522-529.
Hart et al., J. Med. Chem., 1996, 39, 56-65.
McGuire et al., Biochem. Pharmacol., 1996, 52, 1295-1303.
Muller et al., Nuclear Medicine and Biology, vol. 34, No. 6, Aug. 1, 2007 (Aug. 1, 2007), pp. 603-608, XP022232442, ISSN: 0969-8051.
Birdsall et all, FEBS Letters, vol. 402, Issue 2-3, Jan. 1997, pp. 157-162.
Furuya et al, Nature 2011, vol. 473 (7348), pp. 470-477.
Kamlet et al, PLoS One. 2013, vol. 8 (3), e59187.
Bernard-Gauthier et al, Biomed Res Int., vol. 2014; 2014: 454503.
Elnakat and Ratnam, Adv. Drug Deliv. Rev., 2004, vol. 56, pp. 1067-1084.
Turk et al., Arthritis and Rheumatism, 2002, vol. 45, pp. 1947-1955.
Paulos et al., Adv. Drug Deliv. Rev. 2004, vol. 56, pp. 1205-1217.
Chen et al., Arthritis Research & Therapy, 2005, vol. 7, pp. 310-317.
Hattori et al., Biol. & Pharm. Bull. 2006, vol. 29, pp. 1516-1520.
Chandraseka et al., J. Biomed. Mat. Res., Part A 2007, vol. 82, pp. 92-103.
Varghese et al., Mol. Pharmaceutics 2007, vol. 4, pp. 679-685.

(Continued)

*Primary Examiner* — Michael G. Hartley
*Assistant Examiner* — Sean R Donohue
(74) *Attorney, Agent, or Firm* — Millen, White, Zelano & Branigan, PC; Ryan Pool (57) ABSTRACT

The present invention is directed towards new ¹⁸F-folate radiopharmaceuticals, wherein fluorine-18 is covalently linked to the glutamate portion of a folate or derivative thereof, a method of their preparation, as well as their use in diagnosis and monitoring of therapy of cancer and inflammatory and autoimmune diseases.

20 Claims, 3 Drawing Sheets

(56) References Cited

OTHER PUBLICATIONS

Low et al., Accounts of Chemical Research, 2008, vol. 41, pp. 120-129.
Matteson et al., Clinical and Experimental Rheumatology, 2009, vol. 27, pp. 253-259.
Leamon and Low, Drug Discov. Today, 2001, vol. 6, pp. 44-51.
Leamon and Reddy, Adv. Drug Deliv. Rev., 2004, vol. 56, pp. 1127-1141.
Leamon et al, Bioconjugate Chem. 2005, vol. 16, pp. 803-811.
Ward et al,. J. Drug Target. 2000, vol. 8, pp. 119-123.
Leamon et al, J. Biol. Chem. 1993, vol. 268, pp. 24847-24854.
Leamon and Low, J. Drug Target. 1994, vol. 2, pp. 101-112.
Li et al, Pharm. Res. 1998, vol. 15, pp. 1540-1545.
Zhao and Lee, Adv. Drug Deliv. Rev. 2004, vol. 56, pp. 1193-1204.
Lee and Low, Biochim. Biophys. Acta-Biomembr. 1995, vol. 1233, pp. 134-144.
Gabizon et al, Adv. Drug Deliv. Rev. 2004, vol. 56, pp. 1177-1192.
Konda et al, Magn. Reson. Mat. Phys. Biol. Med. 2001, vol. 12, pp. 104-113.
Siegel et al., J. Nucl. Med. 2003, vol. 44, 700.
Muller et al., J. Organomet. Chem. 2004, 689:4712.
Mathias et al., Nucl. Med. Biol., 2003, vol. 30, No. 7, 725.
Ross et al., Bioconjugate Chem., 2008, vol. 19, 2402.

* cited by examiner

<sup>18</sup>F-LABELLED FOLATES AS PET RADIOTRACERS

This is a continuation of Ser. No. 13/132,329 which is a § 371 national phase application of PCT/EP2009/063258, filed Oct. 12, 2009, which claims priority from European Patent Application No. 08166356.9, filed Oct. 10, 2008.

FIELD OF INVENTION

The present invention is directed towards new $^{18}$F-folate radiopharmaceuticals, wherein fluorine-18 is covalently linked to the glutamate portion of a folate or derivative thereof, a method of their preparation, as well as their use in diagnosis and monitoring of cancer and inflammatory and autoimmune diseases and therapy thereof.

BACKGROUND

Cell-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations as γ-rays or photons or particle emitting radiation, selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury in other e.g. healthy tissues. It is thus of crucial interest to determine and assess cell-specific structures and in particular structures that are present in case of tumors (i.e. cancer) or inflammatory and autoimmune diseases, such as receptors, antigens, haptens and the like which can be specifically targeted by the respective biological vehicles.

The folate receptor (FR) has been identified as one of these structures. The FR is a high-affinity ($K_D<10^{-9}$ M) membrane-associated protein. In normal tissues and organs FR-expression is highly restricted to only a few organs (e.g. kidney, lungs, choroids plexus, and placenta), where it largely occurs at the luminal surface of epithelial cells and is therefore not supplied with folate in the circulation. The FR-alpha is frequently overexpressed on a wide variety of specific cell types, such as epithelial tumours (e.g. ovarian, cervical, endometrial, breast, colorectal, kidney, lung, nasopharyngeal), whereas the FR-beta is frequently overexpressed in leukaemia cells (approx. 70% of acute myelogenous leukaemia (AML) are FR-beta positive). Both may therefore be used as a valuable tumour marker for selective tumour-targeting (Elnakat and Ratnam, Adv. Drug Deliv. Rev. 2004; 56:1067-84). In addition, the FR-beta isoform has been found on activated (but not resting) macrophages. Activated macrophages are involved in inflammatory pathologies such as e.g. rheumatoid arthritis, psoriasis, Crohn's disease, ulcerative colitis, systemic lupus erythematosus, atherosclerosis, diabetes, osteoarthritis, glomerulonephritis, infections, etc.

The literature reports several preclinical studies of folate-based imaging agents for detection/localization of sites of inflammation as well as folate receptor targeted therapy of theses diseases. Recently, a clinical study has been published that reports the results of imaging studies in patients with rheumatoid arthritis using the FolateScan (Turk et al., Arthritis and Rheumatism 2002, 45, 1947-1955; Paulos et al., Adv. Drug Deliv. Rev. 2004, 56, 1205-1217; Chen et al., Arthritis Research & Therapy 2005, 7, 310-317; Hattori et al., Biol. & Pharm. Bull. 2006, 29, 1516-1520; Chandraseka et al., J. Biomed. Mat. Res. Part A 2007, 82, 92-103; Varghese et al., Mol. Pharmaceutics 2007, 4, 679-685; Low et al. Discovery and development of folic-acid-based receptor targeting for imaging and therapy of cancer and inflammatory diseases 2008, 41, 120-129; Matteson et al., Clinical and Experimental Rheumatology 2009, 27, 253-259).

Folic acid, which is based on a pteridine skeleton conjugated through a benzoylamino moiety to a glutamate, and its derivatives have thus been intensively studied over the past 15 years as targeting agents for the delivery of therapeutic and/or diagnostic agents to cell populations bearing folate receptors in order to achieve a selective concentration of therapeutic and/or diagnostic agents in such cells relative to normal cells.

Various folic acid derivatives and conjugates are known and have been (pre) clinically evaluated, including folate radiopharmaceuticals (Leamon and Low, Drug Discov. Today 2001; 6:44-51; U.S. Pat. No. 4,276,280), fluorinated folate chemotherapeutics (U.S. Pat. No. 4,628,090), folate-conjugates with chemotherapeutic agents (Leamon and Reddy, Adv. Drug Deliv. Rev. 2004; 56:1127-41; Leamon et al, Bioconjugate Chem. 2005; 16:803-11), with proteins and protein toxins (Ward et al, J. Drug Target. 2000; 8:119-23; Leamon et al, J. Biol. Chem. 1993; 268:24847-54; Leamon and Low, J. Drug Target. 1994; 2:101-12), with antisense oliconucleotides (Li et al, Pharm. Res. 1998; 15:1540-45; Zhao and Lee, Adv. Drug Deliv. Rev. 2004; 56:1193-204), with liposomes (Lee and Low, Biochim. Biophys. Acta-Biomembr. 1995; 1233:134-44; Gabizon et al, Adv. Drug Deliv. Rev. 2004; 56:1177-92), with hapten molecules (Paulos et al, Adv. Drug Deliv. Rev. 2004; 56:1205-17), with MRI contrast agents (Konda et al, Magn. Reson. Mat. Phys. Biol. Med. 2001; 12:104-13) etc.

Folate radiopharmaceuticals can be in particular very useful for an improved diagnosis and evaluation of the effectiveness of cancer and inflammatory and autoimmune disease therapy. This may include assessment and/or prediction of a treatment response and consequently improvement of radiation dosimetry. Typical visualization techniques suitable for radioimaging are known in the art and include positron emission tomography (PET), planar or single photon emission computerized tomography (SPECT) imaging, gamma cameras, scintillation, and the like.

Both PET and SPECT use radiotracers to image, map and measure activities of target sites of choice. Yet while PET uses positron emitting nuclides which require a nearby cyclotron, SPECT uses single photon emitting nuclides which are available by generator systems, which may make its use more convenient. However SPECT provides less sensitivity than PET and beside a few approaches quantification methods are lacking. In case of PET, the positron annihilation results in two gamma rays of 511 keV which provide the basis for well developed quantification methods. Thus PET is one of the most sophisticated functional imaging technologies to assess regional uptake and affinity of ligands or metabolic substrates in brain and other organs and thus provides measures of imaging based on metabolic activity. This is for example achieved by administering a positron emitting isotope to a subject, and as it undergoes radioactive decay the gamma rays resulting from the positron/electron annihilation are detected by the PET scanner.

Factors that need to be considered in the selection of a suitable isotope useful for PET include sufficient half-life of the positron-emitting isotope to permit preparation of a diagnostic composition optionally in a pharmaceutically acceptable carrier prior to administration to the patient, and sufficient remaining half-life to yield sufficient activity to permit extra-corporeal measurement by a PET scan. Furthermore, a suitable isotope should have a sufficiently short half-life to limit patient exposure to unnecessary radiation. Typically, a suitable radiopharmaceutical for PET may be based on a metal isotope, such as gallium or copper. These two require however a chelator for entrapment of the metal, which may have an effect on steric and chemical properties. Alternatively a radiopharmaceutical may be based on a covalently linked isotope which provides minimal structural alteration. Radionuclides used for covalent attachment and which could be suitable for PET scanning are typically isotopes with short half lives such as $^{11}$C (ca. 20 min), $^{13}$N (ca. 10 min), $^{15}$O (ca. 2 min), $^{18}$F (ca. 110 min).

To date, a number of chelate-based folate radiopharmaceuticals have been synthesized and successfully evaluated as diagnostic agents for imaging folate receptor-positive tumors. The most widely studied derivatives were labeled either with $^{111}$In and $^{99m}$Tc (Siegel et al., J. Nucl. Med. 2003, 44:700; Müller et al., J. Organomet. Chem. 2004, 689:4712) for SPECT or with $^{68}$Ga for PET (Mathias et al., Nucl. Med. Biol. 2003, 30(7):725). However, all of the above need a suitable chelating agent, which is typically linked to folic acid through its glutamate portion.

Thus a folate radiopharmaceutical having a covalently linked isotope would be of great interest. In particular a $^{18}$F-labeled folate radiopharmaceutical would be most suitable for PET Imaging because of its excellent imaging characteristics which would fulfil all of the above considerations. Compared with other suitable radionuclides ($^{11}$C, $^{13}$N, $^{15}$O), $^{18}$F is very useful because of its long half-life of approximately 110 minutes and because it decays by emitting positrons having the lowest positron energy, which allows for the sharpest images with a high-resolution PET. Furthermore, the longer half-life of $^{18}$F also allows for syntheses that are more complex and satellite distribution to PET centers with no radiochemistry facilities.

Yet, to date, there have been only few $^{18}$F-labeled folic acid derivatives reported in the literature (Bettio et al., J. Nucl. Med., 2006, 47(7), 1153; Ross et al., Bioconjugate Chem., 2008, 19, 2402; WO 2006/071754; WO 2008/098112; WO 2008/125613; WO 2008/125615; WO 2008/125617), in addition to few reports on folate derivatives labeled with isotopes having much longer half-lives, such as $^{131}$I (60 days) and $^{125}$I (8 days: U.S. Pat. Nos. 4,276,280, 4,298,735) and $^{75}$Se (120 days: GB 1501119, U.S. Pat. No. 4,202,976). Moreover, some of the methodologies suffer from drawbacks including time-consuming radiosyntheses giving only low radiochemical yields of less than 5% (Bettio et al., J. Nucl. Med., 2006, 47(7), 1153) or unfavoruable pharmacokinetics for molecular imaging purposes (Ross et al., Bioconjugate Chem., 2008, 19, 2402). Thus, there is still a need for specific radiopharmaceuticals suitable for metabolic imaging of tumors to improve diagnosis and treatment of cancer and inflammatory and autoimmune diseases.

Applicants have now found efficient and versatile methods for production of new $^{18}$F-labeled folate radiopharmaceuticals wherein fluorine-18 is linked to the glutamate portion of a folate or derivative thereof. The present method is highly effective giving the desired $^{18}$F-folate in good yields to meet the expectations for a clinical application in humans. In addition, the new radiosynthesis is applicable in an automated synthesis module which allows a fast and convenient labeling procedure which meets the requirements of GMP guidelines. Preliminary in-vitro and in-vivo studies suggested their suitability as powerful diagnostic agents for FR-positive tumours.

SUMMARY OF THE INVENTION

The present invention is in a first aspect directed to new $^{18}$F-folate radiopharmaceuticals (hereinafter also called compounds of the invention), wherein fluorine-18 is linked to the glutamate portion of a folate or derivative thereof.

In one specific embodiment, the new folate radiopharmaceuticals are compounds of formula I, wherein
P is a pteroyl group or derivative thereof,
$X_a$, $X_b$ are independently of each other C, N, O, S,
$R_a$, $R_b$ are independently of each other H or straight-chain or branched $C_1$-$C_{12}$ alkyl, $C_3$-$C_6$ cycloalkyl, $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —SO$_2$—, —CH=CH—, —C≡C—, wherein R' is H or $C_1$-$C_6$ alkyl; and
$Z_1$, $Z_2$ are independently of each other H or $^{18}$F, with the proviso that one of $Z_1$ and $Z_2$ is $^{18}$F.

In another specific embodiment, the new folate radiopharmaceuticals are compounds of formula II wherein
$X_1$ to $X_5$ are independently of each other C or N,
$R_1$ and $R_2$ are independently of each other H, Hal, —OR', —NR"R''', $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy) carbonyl, and ($C_1$-$C_{12}$ alkylamino)carbonyl, wherein R' is H or $C_1$-$C_6$ alkyl, and wherein R" and R''' are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl,
$R_3$, $R_4$ are independently of each other H, formyl, trifluoroacetyl, iminomethyl, nitroso, straight chain or branched $C_1$-$C_{12}$ alkyl, which is unsubstituted or substituted by at least one CN, Hal, or $NO_2$, and wherein one or more of embedded, non-adjacent CH$_2$ groups may independently be replaced by —O—, —CO—, —CO—O—, —CO—NR'—, —SO$_2$—, —CH=CH—, —C≡C—, wherein R' is H or C$_1$-C$_6$ alkyl, or R$_3$ and R$_4$ form together a C$_1$ or C$_2$-bridge between X$_3$ and X$_5$, R$_5$ is H, C$_1$-C$_{12}$ alkyl, C$_1$-C$_{12}$ alkoxy, C$_1$-C$_{12}$ alkanoyl, C$_2$-C$_{12}$ alkenyl, C$_2$-C$_{12}$ alkynyl, (C$_1$-C$_{12}$ alkoxy)carbonyl, and (C$_1$-C$_{12}$ alkylamino) carbonyl, m is 0 or 1, p is 0, 1 or 2, q has a value of 1 to 7

X$_a$, X$_b$ are independently of each other C, N, O, S,

R$_a$, R$_b$ are independently of each other H or straight-chain or branched C$_1$-C$_{12}$ alkyl, C$_3$-C$_6$ cycloalkyl, C$_5$-C$_{14}$ aryl or C$_5$-C$_{14}$ heteroaryl, which independently of each other are unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —SO$_2$—, —CH=CH—, —C≡C—, wherein R' is H or C$_1$-C$_6$ alkyl; and Z$_1$, Z$_2$ are independently of each other H or $^{18}$F, with the proviso that one of Z$_1$ and Z$_2$ is $^{18}$F.

In a further aspect the present invention is directed to a method of their preparation.

In another aspect the present invention is directed to pharmaceutical compositions of the compounds of the invention.

In yet another aspect the present invention is directed to the use in diagnosis and monitoring of therapy of cancer and inflammatory and autoimmune diseases in vitro or in vivo.

In one embodiment, the present invention is directed towards uses of the compounds of the invention for diagnostic imaging of a cell or population of cells expressing a folate-receptor.

More specifically the present invention includes methods for diagnostic imaging of a cell or population of cells expressing a folate-receptor, which includes for example methods for in vitro detection of a cell expressing the folate receptor, for example a tumor cell or an activated macrophage, in a tissue sample. Such methods may also be performed in vivo.

Thus, in a further embodiment the present invention is directed towards uses of the compounds of the invention for convenient and effective administration to a subject in need for diagnostic imaging and/or monitoring of therapy of cancer and inflammatory and autoimmune diseases. The subject of the methods of the present invention is preferably a mammal, such as an animal or a human, preferably a human.

Such methods of the invention may be performed in combination with any other methods of diagnosis or therapy of cancer and inflammatory and autoimmune diseases including methods using other already developed diagnostic and/or therapeutic agents and utilizing x-ray computed tomography (CT), magnetic resonance imaging (MRI), functional magnetic resonance imaging (fMRI), single photon emission computed tomography (SPECT), optical imaging, and ultrasound.

Other features and advantages of the invention will be apparent from the following detailed description thereof and from the claims.

DETAILED DESCRIPTION OF THE INVENTION

The present invention is in a first aspect directed to new $^{18}$F-folate radiopharmaceuticals (hereinafter also called compounds of the invention), wherein fluorine-18 is linked to the glutamate portion of a folate or derivative thereof.

The term "folate" as used herein, comprises compounds based on a pteroyl group, which is coupled through a peptide bond to a glutamic acid (or derivative thereof). The term "pteroyl" as used herein represents a condensed pyrimidine heterocycle, which is linked to an aminobenzoyl moiety. As used herein a "condensed pyrimidine heterocycle" includes a pyrimidine fused with a further 5- or 6-membered heterocycle, resulting in a pteridine (i.e. a fused 6-6 heterocycle) or a pyrrolopyrimidine bicycle (i.e. a fused 6-5 heterocycle). Derivatives of a condensed pyrimidine heterocycle include carbocyclic derivatives such as indoles, and isoindoles, quinolines and isoquinolines, and the like. As used herein a "condensed pyrimidine heterocycle, which is linked to an aminobenzoyl moiety" also includes three fused ring systems, i.e. wherein the amino group of the aminobenzoyl moiety forms a further fused ring with the condensed pyrimidine heterocycle, resulting in a fused 6-6-6, 6-6-5, 6-5-6, or 6-5-5 heterocycle. Preferred representatives of folates as used herein are based on a folate skeleton, i.e. pteroyl-glutamic acid resp. N-[4-[[(2-amino-1,4-dihydro-4-oxo-6-pteridinyl)methyl]amino]benzoyl]-L-(or D-)glutamic acid, and derivatives thereof and includes optionally substituted folic acid, folinic acid, pteropolyglutamic acid, 5,10-methenyl-5,6,7,8-tetrahydrofolate and folate receptor-binding pteridines such as tetrahydropterins, dihydrofolates, tetrahydrofolates, and their deaza and dideaza analogs. Folic acid, 5-methyl-(6S)-tetrahydrofolic acid and 5-formyl-(6S)-tetrahydrofolic acid are the preferred basic structures used for the compounds of this invention. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. Preferred deaza analogs compounds include N-[4-[2-[(6R)-2-amino-1,4,5,6,7,8-hexahydro-4-oxopyrido[2,3-d]pyrimidin-6-yl]ethyl]benzoyl]-L-glutamic acid (Lometrexol) and N-[4-[1-[(2,4-diamino-6-pteridinyl) methyl]propyl]benzoyl]-L-glutamic acid (Edatrexate).

More specifically, the new folate radiopharmaceuticals are compounds of formula I, wherein

P is a pteroyl group or derivative thereof,

X$_a$, X$_b$ are independently of each other C, N, O, S, $R_a$, $R_b$ are independently of each other H or straight-chain or branched $C_1$-$C_{12}$ alkyl, $C_3$-$C_6$ cycloalkyl, $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, —C≡C—, wherein R' is H or $C_1$-$C_6$ alkyl; and $Z_1$, $Z_2$ are independently of each other H or $^{18}F$, with the proviso that one of $Z_1$ and $Z_2$ is $^{18}F$.

In another specific embodiment, the new folate radiopharmaceuticals are compounds of formula II

II wherein $X_1$ to $X_5$ are independently of each other C or N, $R_1$ and $R_2$ are independently of each other H, Hal, —OR', —NR''R''', $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy) carbonyl, and ($C_1$-$C_{12}$ alkylamino)carbonyl, wherein R' is H or $C_1$-$C_6$ alkyl, and wherein R'' and R''' are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl, $R_3$, $R_4$ are independently of each other H, formyl, trifluoroacetyl, iminomethyl, nitroso, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl, or $R_3$ and $R_4$ form together a $C_1$ or $C_2$-bridge between $X_3$ and $X_5$, $R_5$ is H, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, and ($C_1$-$C_{12}$ alkylamino) carbonyl, m is 0 or 1, P is 0, 1 or 2, q has a value of 1 to 7

$X_a$, $X_b$ are independently of each other C, N, O, S, $R_a$, $R_b$ are independently of each other H or straight-chain or branched $C_1$-$C_{12}$ alkyl, $C_3$-$C_6$ cycloalkyl, $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, —C≡C—, wherein R' is H or $C_1$-$C_6$ alkyl; and

$Z_1$, $Z_2$ are independently of each other H or $^{18}F$, with the proviso that one of $Z_1$ and $Z_2$ is $^{18}F$.

It is understood, that the abbreviations "N" and "C" are representative for all possible degrees of saturation, i.e. N includes —NH— and —N= linkages and C includes —$CH_2$— and —CH= linkages.

It is further understood, that $(H)_q$ represents all H substituents on the indicated ring (i.e. on $X_3$, C6, C7 and $X_4$). For example q=5 for a fully saturated unsubstituted analog ($X_3$=$X_4$=N, p=0) or q=7 for a fully saturated unsubstituted 5,8-dideaza analog ($X_3$=$X_4$=C, p=0) and q=1 for a fully unsaturated analog with $X_3$=$X_4$=N, p=0.

It is further understood that all isomers, including enantiomers, diastereoisomers, rotamers, tautomers and racemates of the compounds of formula I are contemplated as being part of this invention. The invention includes stereoisomers in optically pure form and in admixture, including racemic mixtures. Isomers can be prepared using conventional techniques, either by reacting optically pure or optically enriched starting materials or by separating isomers of a compound of formula I. This applies specifically to any amino acid groups present in a compound of formula I (and subsequent formulas), which may be present in the natural L- or non-natural D-form. In a specific embodiment, unless specified otherwise the term "glutamic acid" or "glutamate portion" always refers to both the natural L- and non-natural D-isomer.

In another specific embodiment, the new folate radiopharmaceuticals are compounds of formulae IIIa, IIIb, IVa, or IVb,

IIIa

IIIb

IVa

IVb wherein $X_1$ to $X_5$ are independently of each other C or N, $R_1$ and $R_2$ are independently of each other H, Hal, —OR', —NR"R"', $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy) carbonyl, and ($C_1$-$C_{12}$ alkylamino)carbonyl, wherein R' is H or $C_1$-$C_6$ alkyl, and wherein R" and R"' are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl, $R_3$, $R_4$ are independently of each other H, formyl, trifluoroacetyl, iminomethyl, nitroso, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl, or $R_3$ and $R_4$ form together a $C_1$ or $C_2$-bridge between $X_3$ and $X_5$, $R_5$ is H, CN, Hal, $NO_2$, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino) carbonyl, m is 0 or 1, p is 0, 1 or 2, q has a value of 1 to 7, $X_a$, $X_b$ are independently of each other C, N, O, S, and $R_a$, $R_b$ are independently of each other H or straight-chain or branched $C_1$-$C_{12}$ alkyl, $C_3$-$C_6$ cycloalkyl, $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, —C≡C—, wherein R' is H or $C_1$-$C_6$ alkyl.

Preferably, $R_1$ and $R_2$ may independently of each other be H, alkyl, —$OR_5$, —NR"R"', more preferably —OR', —NR"R"', wherein R' represents H or $C_1$-$C_6$ alkyl, and wherein R" and R"' are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl.

Preferably, $R_3$ is H, formyl, $C_1$-$C_{12}$ alkyl or $C_1$-$C_{12}$ alkanoyl.

Preferably, $R_4$ is H, formyl, nitroso, $C_1$-$C_6$ alkyl, $C_1$-$C_6$ alkoxy, or $C_1$-$C_6$ alkanoyl.

Preferably, $R_3$ and $R_4$ form together a $C_1$ or $C_2$-bridge between $X_3$ and $X_5$.

Preferably, $R_5$ is H, CN, Hal, $NO_2$, $C_1$-$C_{12}$ alkyl, $C_1$-$C_{12}$ alkoxy, $C_1$-$C_{12}$ alkanoyl, or ($C_1$-$C_{12}$ alkoxy) carbonyl, more preferably H, CN, Hal, $NO_2$, or $C_1$-$C_8$ alkyl.

Preferably, $X_a$ and $X_b$ are C, N, O most preferably O.

Preferably $R_a$ and $R_b$ are H or straight-chain or branched $C_1$-$C_{12}$ alkyl or $C_5$-$C_{14}$ aryl, which independently of each other are, which is unsubstituted or substituted by at least one Hal, and wherein one or more of embedded, non-adjacent $CH_2$ groups may independently be replaced by —O—, —CO—, —CO—O—, —$SO_2$—, —CH=CH—.

In a specific embodiment $R_a$ and $R_b$ may independently represent a natural or non-natural amino acid.

The term "natural amino acid" indicates one of the natural L-amino acids found in the natural proteins (Gly, Ala, Val, Leu, Ile, Ser, Thr, Lys, Arg, Asp, Asn, Glu, Gln, Cys, Met, Phe, Tyr, Pro, Trp and His) as well as polymeric forms thereof. Preferred natural amino acids include glutamic acid and polymeric forms thereof such as polyglutamate. The term "non-natural amino acid" refers to both optical isomers of natural α-amino acids, such as D-glutamic acid, as well as modified natural α-amino acids such as chemical derivatives or polymeric forms thereof. Examples of such modifications include, but are not limited to: (i) functional group transformation caused by introduction of a functional group (such as alkylation, esterification, halogenation or amination), oxidation, reduction, addition or dissociation, (ii) introduction of a sugar compound (monosaccharide, disaccharide, oligosaccharide or polysaccharide) or a lipid compound, (iii) phosphorylation, (iv) biotinylation, and the like. Specific examples include e.g., hydroxyproline, α-carboxyglutamate, methionine sulfoxide, methionine methyl sulfonium and O-phosphoserine; N-alkyl, preferably N-methyl amino acids, e.g., N-methyl-valine, N-methyl-isoleucine, N-methyl-leucine, N-methyl-alanine; compounds in which a methylene residue was added to the amino acid backbone, e.g., homoserine, homoleucine, homoisoleucine, homolysine, or in which a methylene residue was deleted from the amino acid backbone, e.g., norvaline (Nva), norleucine (Nle); ornithine (2,5-diamino pentanoic acid), citrulline (2-amino-5-(carbamoylamino)pentanoic acid), diaminobutyric acid (DAB), 2-methyl-alanine.

Those skilled in the art recognize that numerous other unnatural amino acids can be synthesized and utilized in the context of the present invention.

One specific embodiment of the compounds of the invention includes for example compounds wherein

(a) $X_1$ to $X_5$ are N, $R_1$ is $NY_1Y_2$, $R_2$ is O, $R_4$ is $Y_3$, m is 1, p is 0 or 1 and q is 1 or 3, or (b) $X_1$ to $X_5$ are N, $R_1$ is $NY_1Y_2$, $R_2$ is $NH_2$, $R_4$ is $Y_3$, m is 1, p is 0 and q is 1.

Thus, in a further specific embodiment the present invention is for example directed to compounds of formulae Va, Vb, VIa or VIb, Va Vb VIa VIb wherein, $X_a$, $X_b$ are independently of each other C, N, O, S, $R_a$, $R_b$ are independently of each other H or straight-chain or branched $C_1$-$C_{12}$ alkyl, $C_3$-$C_6$ cycloalkyl, $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, —C≡C—, wherein R' is H or $C_1$-$C_6$ alkyl;

$Y_1$, $Y_2$ are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl, and $Y_3$ is selected from H, formyl, trifluoroacetyl, nitroso, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl.

Preferably, $Y_3$ is H, formyl, nitroso, $C_1$-$C_6$ alkyl, $C_1$-$C_6$ alkoxy, or $C_1$-$C_6$ alkanoyl.

In another specific embodiment, the present invention is directed towards a compound according to formula 1 having formulae VIIa, VIIb, VIIIa or VIIIb,

VIIa

VIIb

VIIIa

VIIIb wherein, $X_a$, $X_b$ are independently of each other C, N, O, S, $R_a$, $R_b$ are independently of each other H or straight-chain or branched $C_1$-$C_{12}$ alkyl, $C_3$-$C_6$ cycloalkyl, $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, —C≡C—, wherein R' is H or $C_1$-$C_6$ alkyl;

$Y_1$, $Y_2$ are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl,

$R_3$ is H, formyl, iminomethyl, nitroso, $C_1$-$C_{12}$ alkyl, $C_1$-$C_{12}$ alkoxy, $C_1$-$C_{12}$ alkanoyl, halosubstituted $C_1$-$C_{12}$ alkanoyl, and $Y_3$ is selected from H, formyl, trifluoroacetyl, nitroso, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl, or $R_3$ and $Y_3$ form together a $C_1$ or $C_2$-bridge between the two N-atoms to which they are attached to.

Preferably, $Y_3$ is H, formyl, nitroso, $C_1$-$C_6$ alkyl, $C_1$-$C_6$ alkoxy, or $C_1$-$C_6$ alkanoyl.

In another specific embodiment, the present invention is directed towards a compound according to formula 1 having formulae IXa, IXb, Xa or Xb, wherein,
$X_a$, $X_b$ are independently of each other C, N, O, S,
$R_a$, $R_b$ are independently of each other H or straight-chain or branched $C_1$-$C_{12}$ alkyl, $C_3$-$C_6$ cycloalkyl, $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, —C≡C—, wherein R' is H or $C_1$-$C_6$ alkyl;
$Y_1$, $Y_2$ are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl,
$R_3$ is H, formyl, iminomethyl, nitroso, $C_1$-$C_{12}$ alkyl, $C_1$-$C_{12}$ alkoxy, $C_1$-$C_{12}$ alkanoyl, halosubstituted $C_1$-$C_{12}$ alkanoyl, and
$Y_3$ is selected from H, formyl, trifluoroacetyl, nitroso, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or $C_1$-$C_6$ alkyl, or
$R_3$ and $Y_3$ form together a $C_1$ or $C_2$-bridge between the two N-atoms to which they are attached to.

Preferably, $Y_3$ is H, formyl, nitroso, $C_1$-$C_6$ alkyl, $C_1$-$C_6$ alkoxy, or $C_1$-$C_6$ alkanoyl.

The term "alkyl", when used singly or in combination, refers preferably to straight chain or branched alkyl groups containing 1 to 12 carbon atoms, such as methyl, ethyl, propyl, isopropyl, butyl, sec-butyl, isobutyl, t-butyl, pentyl, isopentyl, neopentyl, hexyl, heptyl, octyl, nonyl, decyl, undecyl, dodecyl and the like. More preferred alkyl groups contain 1 to 8, more preferably 1 to 4 carbon atoms.

As used herein, the term "alkenyl", singly or in combination with other groups, refers to straight chain or branched alkyl groups containing 2 to 12 carbon atoms, such as methylene, ethylene, propylene, isopropylene, butylene, t-butylene, sec-butylene, isobutylene, amylene, isoamylene, pentylene, isopentylene, hexylene and the like. The preferred alkenyl groups contain 2 to 6 carbon atoms.

The term "alkynyl" as used herein refers to a linear or branched chain of carbon atoms with one or more carbon-carbon triple bonds. The preferred alkynyl groups contain 2 to 12, more preferably 2 to 6 carbon atoms.

The term "alkoxy" as used herein refers to alkyl, as defined above, substituted with oxygen, such as methoxy, ethoxy, propoxy, isopropoxy, butoxy, tert-butoxy and the like.

The term "alkanoyl" as used herein refers to formyl, or alkyl, as defined above, terminally-substituted with a carbonyl such as acetyl, propanoyl, butanoyl, pentanoyl and the like.

The term "alkylamino" as used herein refers to alkyl, as defined above, substituted with nitrogen, including both monoalkylamino such as methylamino, ethylamino, propylamino, tert-butylamino, and the like, and dialkylamino such as dimethylamino, diethylamino, methylpropylamino, and the like.

The term "halo" as used herein refers to any Group 17 element and includes fluoro, chloro, bromo, iodo, and astatine(o).

The term "($C_3$-$C_6$)cycloalkyl" as used herein alone or in combination with other groups includes saturated or partially unsaturated cyclic hydrocarbon groups having 1 ring of a total of 3 to 6 carbons, such as cyclopropyl, cyclobutyl, cyclopentyl, cyclohexyl.

The term "($C_5$-$C_{14}$)aryl" as used herein alone or in combination with other groups refers to mono- and bicyclic aromatic groups, such as phenyl, naphthyl, anthracenyl.

The term "($C_5$-$C_{14}$)heteroaryl" as used herein alone or in combination with other groups, means a mono- or bicyclic radical having at least one aromatic ring containing one, two, or three ring heteroatoms selected from N, O and S, the remaining ring atoms being C, such as pyridyl, furyl, imidazolyl, benzimidazolyl, pyrimidinyl, thienyl, quinolinyl, indolyl, thiazolyl.

In a further aspect the present invention also provides a method of synthesizing a compound of the invention. Clearly, the introduction of a $^{18}F$ moiety should occur as late in the synthesis as possible due to its decaying nature. Thus, applicants have found that the compounds of the invention may be obtained in an effective manner by a process which comprises (i) activating the position to be labelled in the suitably protected glutamic acid portion, (ii) coupling the activated glutamic acid with pteroic acid or a derivative thereof and (iii) finally substituting the activating group with $^{18}$F. If desired, steps (i) and (ii) may be reversed.

A synthetic pathway using fluorinated glutamate residues as starting material and subsequent coupling with a pteroyl group may be used to obtain $^{19}$F-labeled compounds as reference compounds, while an analogous synthesis using a $^{18}$F-labeled glutamic acid (see e.g. WO 2008/052788) and subsequent coupling with a pteroyl group is disadvantageous with respect to the half life of $^{18}$F isotope due to time consuming reaction steps (e.g. laborious work up and purification procedures).

Activation of the glutamic acid portion may be achieved by introducing any known activating group A that is susceptible to nucleophilic displacement at the 7-position. These include but are not limited to tosylate, mesylate, brosylate, fluorosulfonate, triflate, nonaflate, alkoxy having 1 to 10 carbon atoms, aryloxy having 6 to 12 carbon atoms, trifluoracetate, nitro, bromo, chloro, iodo, and the like, preferably mesylate, tosylate, nosylate and other sulfonates, sulfonium salts and iodonium salts.

In one embodiment the displacement reaction of the activating group by fluorine-18 and subsequent deprotection may be performed in solution in a one-pot procedure.

In another embodiment the activated precursor is bound directly or via a linker to a solid support and reaction with fluorine-18 will yield the labeled compound in solution.

A suitable solid support may be any suitable solid-phase support which is insoluble in any solvents to be used in the process but to which the linker and/or activated precursor can be covalently bound. Examples of a suitable solid support include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel. If necessary a linker is used, which may be any suitable organic group which serves to space the reactive site sufficiently from the solid support structure so as to maximise reactivity. Suitably, a linker comprises up to four aryl groups (suitably phenyl) and/or a C(1-16)alkyl (preferably C(1-6)alkyl) or C(1-16)haloalkyl (preferably C(1-6) haloalkyl), typically C(1-16)fluoroalkyl (preferably C(1-6) fluoroalkyl), or C(1-16)alkoxy or C(1-16)haloalkoxy (preferably C(1-6)alkoxy or C(1-6)haloalkoxy) typically C(1-16)fluoroalkoxy (preferably C(1-6)fluoroalkoxy), and optionally one to four additional functional groups such as amide or sulphonamide groups.

Treatment of the support-bound activated precursor with fluorine-18 may be effected by treatment with any suitable source of $^{18}$F, such as Na$^{18}$F, K$^{18}$F, Cs$^{18}$F, tetraalkylammonium $^{18}$F fluoride, tetraalkylphosphonium $^{18}$F fluoride or electrochemically bound $^{18}$F fluoride. To increase the reactivity of the fluoride, a phase transfer catalyst such as 4,7,13,16,21,24 hexaoxa-1,10-diazabicyclo[8,8,8] hexacosane may be added and the reaction performed in a non protic solvent or in a combination of a non protic solvent and sterically hindered alcohols, such as tert.-butanol, tert.-amyl-alcohol and the like. The treatment with fluorine-18 is suitably effected in the presence of a suitable organic solvent such as acetonitrile, dimethylformamide, dimethylsulphoxide, tetrahydrofuran, dioxan, 1,2 dimethoxyethane, sulpholane, N-methylpyrolidinineone, at a temperature from 15° C. to 180° C., preferably at elevated temperature. On completion of the reaction, the $^{18}$F-labeled compound dissolved in the solvent is conveniently separated from the solid-phase by filtration.

In a further aspect the present invention provides uses of folate radiopharmaceuticals of the invention for convenient and effective administration to a subject in need for diagnostic imaging.

Thus the present invention provides a method for diagnostic imaging of a cell or population of cells expressing a folate-receptor, said method comprising the steps of administering at least one folate radiopharmaceutical of the invention in a diagnostic imaging amount, and obtaining a diagnostic image of said cell or population of cells.

Such imaging may be performed on a cell or population of cells expressing a folate-receptor in vitro or in vivo.

Thus, the present invention provides a method for in vitro detection of a cell expressing the folate receptor in a tissue sample which includes contacting said tissue sample with at least one folate radiopharmaceutical of the invention in effective amounts and for sufficient time and conditions to allow binding to occur and detecting such binding by PET imaging.

In a further aspect the present invention provides uses of folate radiopharmaceuticals of the present invention for convenient and effective administration to a subject in need for diagnostic imaging or monitoring of therapy of cancer and inflammatory and autoimmune diseases.

In another aspect the present invention provides a method for simultaneous diagnosis and therapy, comprising the steps of administering to a subject in need thereof at least one folate radiopharmaceutical of the present invention in a diagnostically effective amount in combination with a therapeutically active, and obtaining a diagnostic image of said tissues to follow the course of treatment.

The subject of the methods of the present invention is preferably a mammal, such as an animal or a human, preferably a human.

The dosage depends on the nature of the effect desired, such as the form of diagnosis or therapy, on the kind and frequency of treatment, on the diagnostic instrumentation, on the form of application of the preparation, and on the age, weight, nutrition and condition of the recipient, kind of concurrent treatment, if any.

However, the most preferred dosage can be tailored to the individual subject, as is understood and determinable by one of skill in the art, without undue experimentation. This typically involves adjustment of a standard dose, e.g., reduction of the dose if the patient has a low body weight.

Treatment can commence with a smaller amount, below the optimum amount, which can be increased in order to achieve the optimum effect.

The imaging procedure in the PET scanner takes place from within minutes to 2-4 hours after administration of the radiotracer.

The schedule depends on the imaging target and kinetics of the radiotracer as well as the desired information.

The preferred route of administration of the folate radiopharmaceuticals of the present invention is by intraveneous injection.

The suitable forms for injection include sterile aqueous solutions or dispersions of the above mentioned folate radiopharmaceuticals of the present invention. Typically the radiopharmaceutical will be formulated in physiological buffer solutions.

The folate radiopharmaceuticals can undergo sterilization by any art recognized technique, including but not limited to, addition of antibacterial of antifungal agents, for example, paraben, chlorobutanol, phenol, sorbic acid, thimerosal, and the like. Preferably they undergo a sterile filtration before administration eliminating the need of additional sterilisation agents.

For a solution to be injected a preferred unit dosage is from about 0.01 mL to about 10 mL. After intravenous administration, imaging of the organ or tumor in vivo can take place, if desired, from within minutes to 2-4 hours after the radiolabeled reagent has been administered to a subject to allow a sufficient amount of the administered dose to accumulate in the targeted area of choice.

The folate radiopharmaceuticals of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell, in a tissue sample which includes contacting said tissue sample with a folate radiopharmaceutical of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any tissue suspected to contain a cell expressing a folate receptor, such as tumour cells, epithelial cells, kidneys, gastrointestinal or the hepatobiliary system, and others. Samples can be sectioned, e.g., with a microtome, to facilitate microscopic examination and observation. Samples can also be fixed with an appropriate fixative either before or after incubation with one of the folate radiopharmaceuticals of the present invention to improve the histological quality of sample tissues.

Time and conditions sufficient for binding of a folate radiopharmaceutical of the present invention to a folate receptor on the cell include standard tissue culture conditions, i.e. samples can be cultured in vitro and incubated with one of the complexes or compositions of the present invention in physiological media. Such conditions are well known to the skilled person. Alternatively, samples can be fixed and then incubated with a folate radiopharmaceutical of the present invention in an isotonic or physiological buffer.

For all applications it is convenient to prepare the compounds of the present invention at, or near, the site where they are to be used.

All of the compounds and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way.

EXAMPLES

Materials and Methods

Nuclear magnetic resonance spectra were recorded with a Varian Mercury Plus 200 (200 MHz) spectrometer. Chemical shifts are reported in parts per million (ppm) relative to tetramethylsilane (0.00 ppm). The following abbreviations are used in the experimental section for the description of $^1$H-NMR spectra: singlet (s), doublet (d), triplet (t), multiplet (m), doublet of doublets (dd). The chemical shifts of complex multiplets are given as the range of their occurrence. HR-ESI-MS were recorded with a Bruker FTMS 4.7 T BioAPEXII (ESI) spectrometer.

Water sensitive reactions were run under argon in flame-dried glass ware. Reactions were monitored by thin layer chromatography (TLC, performed on EM Science 0.25 mm thick, precoated silica gel 60 F-254 glass supported plates) or HPLC. HPLC was performed on a Merck-Hitachi L-7000 system equipped with a L-7400 tunable absorption detector. Analytical HPLC was performed with a Nucleosil column (C18, 5 µm, 4×250 mm, Macherey Nagel) using the following solvent system (1 mL/min): Solvent A: 0.05M aq. NaH2PO4, adjusted to pH 7.0 with 32% NaOH, Solvent B: 800 ml MeOH/200 ml 0.05M $NaH_2PO_4$, 1 mL/min; 0 min, 100% A; 0-30 min, 100-0% A. UV detection at 230 nm. 20 mg of the sample were dissolved in a buffer consisting of 20 g $NaHCO_3$ and g $KHCO_3$ in 1000 ml of water. All chemicals were used as supplied unlike stated otherwise.

Semi-preparative HPLC purification of the γ-[$^{18}$F]fluoro-folic acid was carried out on a RP 18 column, Gemini 5µ C18, 250×10 mm, using a gradient as follows. Solvent A=0.05M phosphate buffer solution (5% methanol), B=methanol, 0-35 min: A: 100%→40%, 35-40 min: A:40%→20%, 50-60 min: A: 20%→100%. Flow: 4 ml/min.

Production of n.c.a. [$^{18}$F]fluoride. N.c.a. [$^{18}$F]fluoride was produced via the $^{18}$O(p,n)$^{18}$F nuclear reaction at a Cyclone 18/9 cyclotron (IBA, Belgium). Isotopically 97% enriched [$^{18}$O]water was irradiated by a 16 MeV proton beam using a 2.1 ml liquid target. The [$^{18}$F]fluoride/[$^{18}$O]water solution was transferred from the target to a manipulator equipped syntheses hotcell using a helium stream.

The [$^{18}$F]fluoride which was trapped on an anion exchange cartridge, was directly eluted into a 10 ml sealed reaction vessel using a solution of tetrabutylammonium hydroxide in methanol (0.7 ml). At 85-90° C. the solvents were removed by vacuum and a stream of nitrogen. Subsequently, 0.8-1.0 ml of dry acetonitrile was added three times and evaporated to dryness.

A γ-Fluoro-folic acid reference standard can be synthesized e.g. according to B. Hart et al, J. Med. Chem., 39, 1996, 56-65. A β-Fluoro-folic acid reference standard can be synthesized in analogy to the same literature using the analogous β-fluoro-glutamic acid which can be synthesized according to e.g. A. Vidal-Cros et al, J. Org. Chem., 54, 498, 1989.

EXPERIMENTAL

Figure 1:
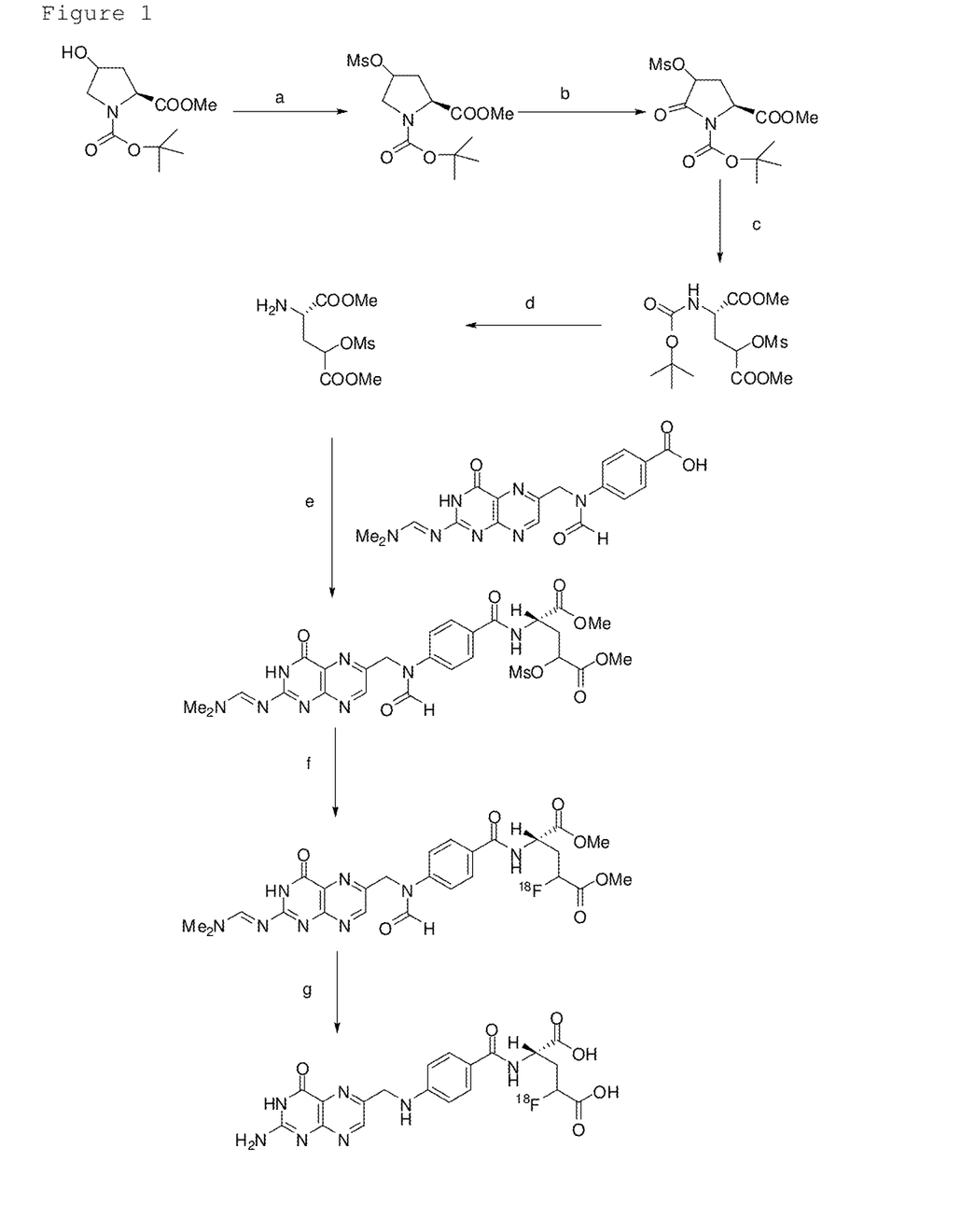
FIG. 1: Synthesis pathway of γ-[$^{18}$F]-compounds.

Synthesis of γ-[$^{18}$F]fluorofolic acid (According to FIG. 1)

EXAMPLE 1

Synthesis of 4-methanesulfonyloxy-pyrrolidine-1,2-dicarboxylic acid-1-tert-butylester-2-methylester
(Step a)

To 10.0 g of 4-hydroxy-pyrrolidine-1,2-dicarboxylic acid-1-tert-butylester-2-methylester (purchased from Bachem) in 200 ml dry dichloromethane were added 4 ml methanesulfonyl chloride. The mixture was cooled to 0° C. and 17 ml triethylamine were added.

The mixture was allowed to warm to room temperature. After 2 hours 500 ml dichloromethane were added. The mixture was washed with 500 ml cold 1 M HCl and two times with 500 ml cold water. The organic layer was evaporated to dryness to give an oil, which was crystallized at 4° C. by addition of 100 ml methyl-tert-butyl ether. The crystals were sucked off, washed two times with 25 ml methyl-tert-butyl ether and dried at 35° C. under vacuum to give 9.27 g of 4-methanesulfonyloxy-pyrrolidine-1,2-dicarboxylic acid-1-tert-butylester-2-methylester. $^1$H-NMR (CDCl$_3$, TMS as internal standard, 200 MHz): δ=5.27 (m, 1H, C(γ)-H), 4.44 (m, 1H, C(α)-H), 3.78 (m, 2H, C(δ)-H$_2$), 3.75 (s, 3H, OCH$_3$), 3.05 (s, 3H, SO$_2$CH$_3$), 2.62 (m, 1H, C(β)-H), 2.19-2.33 (m, 1H, C(β)-H'), 1.46, 1.42 (two s, 9H, OtBu). $^{13}$C-NMR (CDCl$_3$, TMS as internal standard, 200 MHz): δ=172.7, 153.3, 80.9, 77.9, 57.4, 52.5, 52.2, 38.7, 37.5, 28.2. HR-MS: m/z [M+Na]+ calcd. for C$_{12}$H$_{21}$NNaO$_7$S: 346.0931; found: 346.0933.

EXAMPLE 2

Synthesis of 4-methanesulfonyloxy-5-oxo-pyrrolidine-1,2-dicarboxylic acid-1-tert-butylester-2-methylester (Step b)

To 99.8 g of 4-methanesulfonyloxy-pyrrolidine-1,2-dicarboxylic acid-1-tert-butylester-2-methylester in 4000 ml ethyl acetate were added 264 g sodium perjodate and 3.2 g ruthenium (III) chloride in 4000 ml water. The mixture was stirred vigorously for 96 hours at room temperature. After filtration the aqueous layer was separated and extracted two times with 1400 ml ethyl acetate. The ethyl acetate layers were combined and 863 ml iso-propanol were added. After stirring for 30 min., magnesium sulphate was added, filtered off and the residue was evaporated to dryness. The residue was purified by flash chromatography using 1 kg silica gel 60 and ethyl acetate/n-hexane 4.5:5.5. 32.8 g of colourless crystals were obtained which were treated with 100 ml of methyl-tert-butylester at r.t. After cooling to 4° C. the crystals were sucked off, washed with methyl-tert-butylester and dried overnight at 40° C. in vacuum to give 28.9 g of 4-methanesulfonyloxy-5-oxo-pyrrolidine-1,2-dicarboxylic acid-1-tert-butylester-2-methylester. $^1$H-NMR (CDCl$_3$, TMS as internal standard, 200 MHz): δ=5.28-5.38 (m, 1H, C(γ)-H), 4.65-4.70 (m, 1H, C(α)-H), 3.82 (s, 3H, OCH$_3$), 3.30 (s, 3H, SO$_2$CH$_3$), 2.38-2.70 (m, 2H, C((β)-H2), 1.52 (s, 9H, OtBu). $^{13}$C-NMR (CDCl$_3$, TMS as internal standard, 200 MHz): δ=170.7, 167.6, 148.8, 85.1, 75.2, 55.3, 53.2, 40.0, 29.3, 27.9. HR-MS: m/z [M+Na]+ calcd. for C$_{12}$H$_{19}$NNaO$_8$S: 360.0724; found: 360.0728.

EXAMPLE 3

Synthesis of 2-tert-butoxycarbonylamino-4-methanesulfonyloxy-pentanedicarboxylic acid dimethylester (Step c)

To 28.3 g of 4-methanesulfonyloxy-5-oxo-pyrrolidine-1,2-dicarboxylic acid-1-tert-butylester-2-methylester in 354 ml dichloromethane were added 71 ml methanol and 0.58 g potassium carbonate. The mixture was stirred for three hours at room temperature. After filtration the filtrate was evaporated in vacuum and the oily residue was purified by chromatography (90 g silica gel 60, solvent CH$_2$Cl$_2$:MeOH, 99:1 to 95:5) to give 9.8 g of 2-tert-butoxycarbonylamino-4-methanesulfonyloxy-pentanedicarboxylic acid dimethylester as a colourless oil. $^1$H-NMR (CDCl$_3$, TMS as internal standard, 200 MHz): δ=5.3 (s, 1H, NH), 5.14-5.20 (m, 1H, C(γ)-H), 4.50 (m, 1H, C(α)-H), 3.81 (s, 3H, OCH$_3$), 3.78 (s, 3H, OCH$_3$), 3.15 (s, 3H, SO$_2$CH$_3$), 2.32-2.64 (m, 2H, C((β)-H$_2$), 1.45 (s, 9H, OtBu). $^{13}$C-NMR (CDCl$_3$, TMS as internal standard, 200 MHz): δ=171.5, 169.1, 74.4, 74.1, 52.9, 52.7, 50.0, 39.2, 34.2, 28.5. HR-MS: m/z [M+Na]+ calcd. for C$_{13}$H$_{23}$NNaO$_9$S: 392.0986; found: 392.0981.

EXAMPLE 4

Deprotection of 2-tert-butoxycarbonylamino-4-methanesulfonyloxy-pentanedicarboxylic acid dimethylester (Step d)

To a solution of 1 g of 2-tert-butoxycarbonylamino-4-methanesulfonyloxy-pentanedicarboxylic acid dimethylester in 10 ml dichloromethane were added 10 ml of trifluoroacetic acid and stirred for 30 min. at room temperature. The mixture was evaporated to dryness, the residue was dried in vacuum to give 1.8 g of an oily residue which was directly used for synthesis of N$^2$-N,N-dimethylaminomethylen-10-formyl-γ-methanesulfonyloxy-folic acid dimethylester in example 5 without further purification. DC (CH$_2$Cl$_2$/MeOH, 9:1, Ninhydrin), Rf =0.29.

EXAMPLE 5

Synthesis of N$^2$-N,N-dimethylaminomethylene-10-formyl-γ-methanesulfonyloxy-folic acid dimethylester (step e)

To 1.07 g of N$^2$,N,N-dimethylaminomethylene-10-formyl-pteroic acid in 100 ml N,N-dimethylformamide were added 1.03 g of 2-(1H-benzotriazol-1-yl)-1,1,3,3-tetramethyluroniumhexafluorophosphate (=HBTU) and 0.93 ml of N,N-diisopropylethylamine. After 5 min. a solution of 1.8 g of crude 2-amino-4-methanesulfonyloxy-pentanedicarboxylic acid dimethylester trifluoroacetate (crude product from example 4) in 10 ml absolute N,N-dimethylformamide were added. The mixture was stirred for 18 hours at room temperature and evaporated to dryness in vacuum. The residue was dissolved in 50 ml dichloromethane and washed three times with 10 ml of aqueous 5% sodium bicarbonate solution, three times with 10 ml of 5% citric acid and three times with 10 ml of water. After drying the dichloromethane layer over magnesium sulphate it was evaporated to dryness to give 1.2 g of a light yellow foam which was purified by chromatography (120 g silica gel 60, eluent dichloromethane/methanol 95:5) to give 0.3 g of a yellow residue which was further purified by chromatography (30 g silica gel 60, eluent dichloromethane/methanol 95:5) to give 0.16 g of N$^2$-N,N-dimethylaminomethylen-10-formyl-γ-methanesulfonyloxy-folic acid dimethylester (Ms=SO$_2$CH$_3$). HPLC: 94.1% area (UV detection at 230 nm); DC (dichloromethane/methanol 85:15) Rf=0.49. $^1$H-NMR (DMSO-d$_6$, TMS as internal standard, 200 MHz): δ=11.99 (bs, 1H, N$^3$-H), 8.82, 8.78 8.71 (three s, 3H, CHNMe$_2$, CHO, C(7)-H), 7.86 (d, 2H, C(1', 5'), Pte), 7.60 (d, 2H, C(2',4'), Pte), 5.24-5.33 (m, s, 3H, C(6)-H$_2$, C(γ)-H), 4.53-4.67 (m, 1H, c(α)-H), 3.64 (s, 3H, OMe), 3.60 (s, 3H, OMe), 3.24 (s, 3H, NCH$_3$), 3.21 (s, 3H, NCH$_3$), 3.08 (s, 3H, SO$_2$CH$_3$), 2.58-2.29 (m, 2H, C((β)-H$_2$). HR-MS: m/z [M+Na]+ calcd. for C$_{26}$H$_{30}$N$_8$NaO$_{10}$S: 669.1698; found: 669.1706.

EXAMPLE 6

Synthesis of γ-[$^{18}$F]fluorofolic acid by $^{18}$F-fluorination of N$^2$,N,N-dimethylaminomethylene-10-formyl-γ-methanesulfonyloxy-folic acid dimethylester and Subsequent Deprotection (Step f and g)

To the dry tetrabutylammonium [$^{18}$F]fluoride the precursor N$^2$,N,N-dimethylaminomethylen-10-formyl-γ-methanesulfonyloxy-folic acid dimethylester (5.2 mg) in 0.25 ml acetonitrile were added. The mixture was heated to 80-85° C. for 35 min. After cooling, 9 ml water were added and the mixture was passed though a reversed phase cartridge (Sep-Pak® 'C18 plus, Waters AG). The cartridge was washed three times with 10 ml of water and dried 2 min by a stream of nitrogen. The $^{18}$F-labeled protected compound was eluted with 2.5 ml of acetonitrile into another 10 ml sealed reaction vessel. The volume of acetonitrile was reduced to 0.1 ml under reduced pressure, nitrogen stream and slight warming of 80-90° C.

For hydrolysis (step g), 0.5 ml of 1M NaOH solution was added and the mixture was heated to 50° C. for 20 min. After cooling, the mixture was neutralized by 0.5 ml 1M HCl solution. 2.0 ml of HPLC solvent A was added to give the final injection volume for the semi-preparative HPLC purification. The HPLC solvent of the product fraction was evaporated under reduced pressure and a stream of nitrogen at 90° C. For formulation, water for injection and 0.15 M phosphate buffer solution were added to the dry product and the mixture was passed through a sterile filter into a sterile and pyrogen-free vial.

EXAMPLE 7

In Vivo and Ex Vivo Studies Using γ-[$^{18}$F]fluoro-folic acid

γ-[$^{18}$F]fluoro-folic acid was applied in ex vivo biodistribution studies using male NMRI nu/nu mice bearing KB tumor xenografts. ~2 MBq of the radiotracer were injected into each animal. In a blockade group, 200 µg natural folic acid was injected 10 min prior to the radiotracer. The animals were sacrificed 105 min post injection. The folate receptor-positive KB tumors show a high specific uptake of the radiotracer with a ratio of 90.0% specific blockade. Furthermore, a high specific uptake of 86.0% specific blockade was also found in the kidneys, which are known to express the folate receptor.

Figure 2:
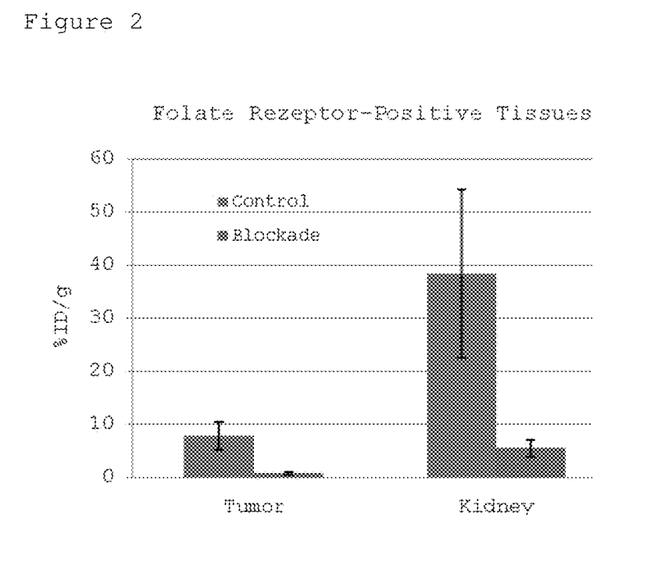
FIG. 2: Specific uptake of the γ-[$^{18}$F]fluoro-folic acid in folate receptor-positive tissues.

FIG. 2 shows the high specific uptake of the γ-[$^{18}$F]fluoro-folic acid in folate receptor-positive tissues, such as tumor and kidney (two bars are shown for each tissue, wherein the left bar represents the control group uptake and the right bar represents the blockade group uptake).

In vivo PET imaging using the γ-[$^{18}$F]fluoro-folic acid was performed in male NMRI nu/nu mice bearing KB tumor xenografts. Ca. 10 MBq of the radiotracer were injected into each animal. In the blockade group, 200 µg natural folic acid was injected 10 min prior to the radiotracer. The PET scans were acquired from 75 min to 105 min post injection.

PET studies using γ-[$^{18}$F]fluoro-folic acid provided excellent images of KB tumor xenografts. Furthermore, the uptake is highly specific and blocked by natural folic acid. A high specific uptake of the radiotracer was also found in the kidney cortex, while no uptake was found in the kidney medulla. This pattern is consistent with the physiological distribution of the folate receptor and points out the high specificity of γ-[$^{18}$F]fluoro-folic acid. Besides the specific tumor and kidney uptake, the γ-[$^{18}$F]fluoro-folic acid also shows radioactivity accumulation in liver cells.

Figure 3:
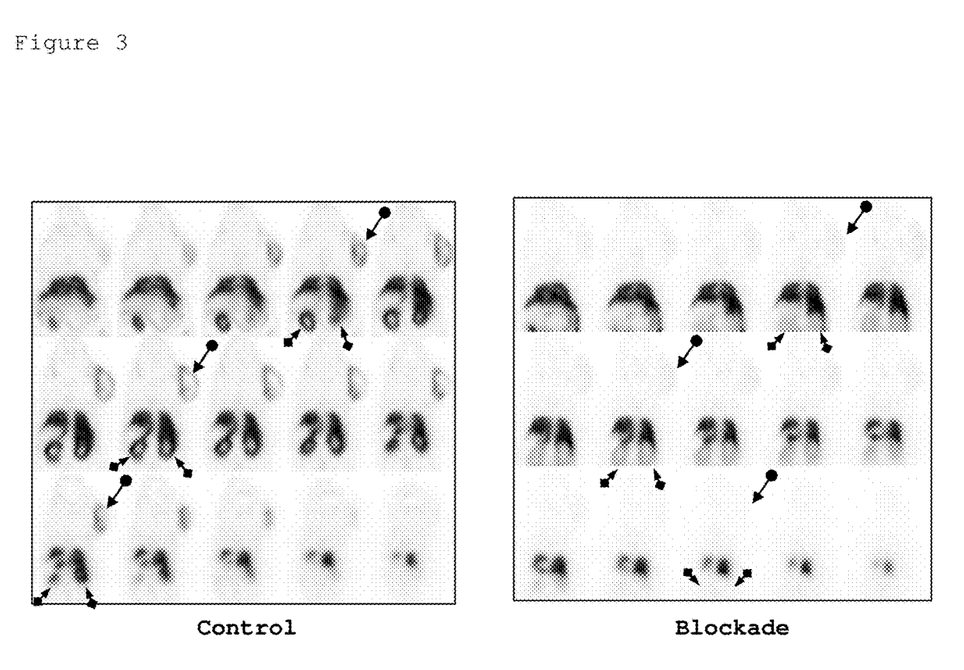
FIG. 3: Representative series of normalized horizontal slices of whole body PET scans using γ-[$^{18}$F]fluoro-folic acid under control and blockade conditions.

FIG. 3 show representative series of normalized horizontal slices of whole body PET scans using γ-[$^{18}$F]fluoro-folic acid under control and blockade conditions. Arrows with circles indicate the tumor site and arrows with squares indicate the kidneys.

The invention claimed is:
1. A compound of formula I, wherein
P is a pteroyl group or a derivative thereof,
$X_a$, $X_b$ are independently of each other C, N, O, or S,
$R_a$, $R_b$ are independently of each other H or straight-chain or branched $C_1$-$C_{12}$ alkyl, $C_3$-$C_6$ cycloalkyl, or $C_5$-$C_{14}$ aryl or $C_5$-$C_{14}$ heteroaryl, which independently of each other are unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —SO$_2$—, —CH═CH—, or —C≡C—,
R' is H or $C_1$-$C_6$ alkyl; and
$Z_1$, $Z_2$ are independently of each other H or $^{18}$F,
with the proviso that one of $Z_1$ and $Z_2$ is $^{18}$F.
2. The compound according to claim 1 having formula II wherein
$X_1$ to $X_5$ are independently of each other C or N,
$R_1$ and $R_2$ are independently of each other H, Hal, —OR', —NR"R'", $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl,
R' is H or $C_1$-$C_6$ alkyl,
R" and R'" are independently of each other H, formyl, or straight chain or branched $C_1$-$C_{12}$ alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH═CH—, or —C≡C—,
$R_3$, $R_4$ are independently of each other H, formyl, trifluoroacetyl, iminomethyl, nitroso, or straight chain or branched $C_1$-$C_{12}$ alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH═CH—, or —C≡C—,
or
$R_3$ and $R_4$ form together a $C_1$ or $C_2$-bridge between $X_3$ and $X_5$,
$R_5$ is H, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl, m is 0 or 1, P is 0, 1 or 2, q has a value of 1 to 7

$X_a$, $X_b$ are independently of each other C, N, O, or S, $R_a$, $R_b$ are independently of each other H or straight-chain or branched $C_1$-$C_{12}$ alkyl, $C_3$-$C_6$ cycloalkyl, or $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, or —C≡C—, and

$Z_1$, $Z_2$ are independently of each other H or $^{18}F$, with the proviso that one of $Z_1$ and $Z_2$ is $^{18}F$.

3. The compound according to claim 1 having formula IIIa, IIIb, IVa, or IVb,

IIIa

IIIb

IVa

IVb wherein $X_1$ to $X_5$ are independently of each other C or N, $R_1$ and $R_2$ are independently of each other H, Hal, —OR', —NR"R'", $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl, R' is H or $C_1$-$C_6$ alkyl, R" and R'" are independently of each other selected from H, formyl, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—, $R_3$, $R_4$ are independently of each other H, formyl, trifluoroacetyl, iminomethyl, nitroso, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—, or $R_3$ and $R_4$ form together a $C_1$ or $C_2$-bridge between $X_3$ and $X_5$, $R_5$ is H, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, or ($C_1$-$C_{12}$ alkylamino)carbonyl, m is 0 or 1, P is 0, 1 or 2, q has a value of 1 to 7, $X_a$, $X_b$ are independently of each other C, N, O, or S, $R_a$, $R_b$ are independently of each other H or straight-chain or branched $C_1$-$C_{12}$ alkyl, C3-C6 cycloalkyl, C5-C14 aryl or C5-C14 heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, or —C≡C—.

4. The compound according to claim 2, wherein $R_1$ and $R_2$ are independently of each other H, $C_1$-$C_{12}$ alkyl, —OR', or —NR"R'", wherein R' represents H or $C_1$-$C_6$ alkyl, R" is H, and R'" is H or $C_1$-$C_6$ alkyl.

5. The compound according to claim 2, wherein $R_3$ is H, formyl, $C_1$-$C_{12}$ alkyl or $C_1$-$C_{12}$ alkanoyl.

6. The compound according to claim 2, wherein $R_3$ is H, formyl, or methyl.

7. The compound according to claim 2, wherein $R_4$ is H, formyl, nitroso, $C_1$-$C_6$ alkyl, $C_1$-$C_6$ alkoxy, or $C_1$-$C_6$ alkanoyl.

8. The compound according to claim 2, wherein $R_4$ is H, formyl, or methyl.

9. The compound according to claim 2, wherein $R_5$ is H, $C_1$-$C_{12}$ alkyl, $C_1$-$C_{12}$ alkoxy, $C_1$-$C_{12}$ alkanoyl, ($C_1$-$C_{12}$ alkoxy)carbonyl, or ($C_1$-$C_{12}$ alkylamino)carbonyl.

10. The compound according to claim 2, wherein $R_5$ is H.

11. The compound according to claim 1 having formula Va, Vb, VIa or VIb, Va Vb VIa VIb VIIIa VIIIb wherein, $X_a$, $X_b$ are independently of each other C, N, O, or S,

$R_a$, $R_b$ are independently of each other H or straight-chain or branched $C_1$-$C_{12}$ alkyl, $C_3$-$C_6$ cycloalkyl, or $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, or —C≡C—, R' is H or $C_1$-$C_6$ alkyl;

$Y_1$, $Y_2$ are independently of each other H, formyl, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—, $Y_3$ is H, formyl, trifluoroacetyl, nitroso, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—.

12. The compound according to claim 1 having formula VIIa, VIIb, VIIIa or VIIIb, VIIa VIIb wherein, $X_a$, $X_b$ are independently of each other C, N, O, or S, $R_a$, $R_b$ are independently of each other H or straight-chain or branched $C_1$-$C_{12}$ alkyl, $C_3$-$C_6$ cycloalkyl, or $C_5$-$C_{14}$ aryl or $C_5$-$C_{14}$ heteroaryl, which independently of each other are unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —$SO_2$—, —CH=CH—, or —C≡C—, R' is H or $C_1$-$C_6$ alkyl;

p is 0, 1 or 2, $Y_1$, $Y_2$ are independently of each other selected from H, formyl, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—, $R_3$ is H, formyl, iminomethyl, nitroso, $C_1$-$C_{12}$ alkyl, $C_1$-$C_{12}$ alkoxy, $C_1$-$C_{12}$ alkanoyl, or halosubstituted $C_1$-$C_{12}$ alkanoyl, and $Y_3$ is H, formyl, trifluoroacetyl, nitroso, or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, or —C≡C—, or $R_3$ and $Y_3$ form together a $C_1$ or $C_2$-bridge between the two N-atoms to which they are attached to.

13. A method for diagnostic imaging of a cell or population of cells expressing a folate-receptor, said method comprising administering at least one compound according to claim 1 in a diagnostic imaging amount, and obtaining a diagnostic image of said cell or population of cells.

14. The method according to claim 13, wherein the diagnostic imaging is performed of a cell or population of cells expressing a folate-receptor in vitro or in vivo.

15. A method for in vitro detection of a cell expressing the folate receptor in a tissue sample which includes contacting said tissue sample with a compound according to claim 1 in effective amounts and for sufficient time and conditions to allow binding to occur and detecting such binding by PET imaging.

16. A method of diagnostic imaging or monitoring a subject comprising (i) administering at least one compound according to claim 1 in a diagnostic imaging amount, and (ii) performing diagnostic imaging by PET by detecting a signal from said at least one compound.

17. A method of monitoring therapy of cancer or an inflammatory or autoimmune disease in a subject comprising (i) administering to a subject in need thereof at least one compound according to claim 1 in a diagnostic imaging amount in combination with a therapeutically active compound, and (ii) performing diagnostic imaging using PET by detecting a signal from said at least one compound to follow the course of therapy of cancer or inflammatory or autoimmune disease.

18. The method of claim 13 performed in combination with a further method of diagnosis or therapy of cancer or inflammatory or autoimmune disease.

19. The compound according to claim 1 wherein $Z_1$ is $^{18}F$ and $Z_2$ is H.

20. The compound according to claim 1 wherein $Z_1$ is H and $Z_2$ is $^{18}F$.

* * * * *